United States Patent [19]

Rudko et al.

[11] Patent Number: 5,200,604
[45] Date of Patent: Apr. 6, 1993

[54] HANDPIECE OPTICAL PROXIMITY DETECTOR FOR DISABLING SURGICAL LASER BEAM

[75] Inventors: Robert I. Rudko, Holliston; Stephen J. Linhares, Taunton, both of Mass.

[73] Assignee: Laser Engineering, Inc., Milford, Mass.

[21] Appl. No.: 741,642

[22] Filed: Aug. 7, 1991

[51] Int. Cl.⁵ .............................................. G01J 1/32
[52] U.S. Cl. ................................... 250/205; 250/561; 219/121.62; 606/12
[58] Field of Search .................. 250/221, 561, 227.11, 250/227.21, 227.29, 214 A, 205; 606/2, 12, 16; 128/397, 398; 219/121.61, 121.62

[56] References Cited

U.S. PATENT DOCUMENTS 4,561,440 12/1985 Kubo et al. ............... 219/121.62
4,622,971 11/1986 Yamamoto et al. ............ 219/121.61
5,071,417 12/1991 Sinofsky ........................ 606/12

FOREIGN PATENT DOCUMENTS 2647618 4/1978 Fed. Rep. of Germany ........ 606/12

Primary Examiner—David C. Nelms
Assistant Examiner—K. Shami
Attorney, Agent, or Firm—Iandiorio & Dingman

[57] ABSTRACT

A proximity detector for the probe of a beam delivery apparatus of a laser system includes a probe having a face for confronting a target surface to be struck by the laser beam; means for directing a gauging light to the target surface; means for sensing the gauging light returning from the target surface to the probe; and means responsive to the means for sensing for generating a control signal representative of the position of the probe relative to the surface to enable the laser system to fire.

12 Claims, 4 Drawing Sheets

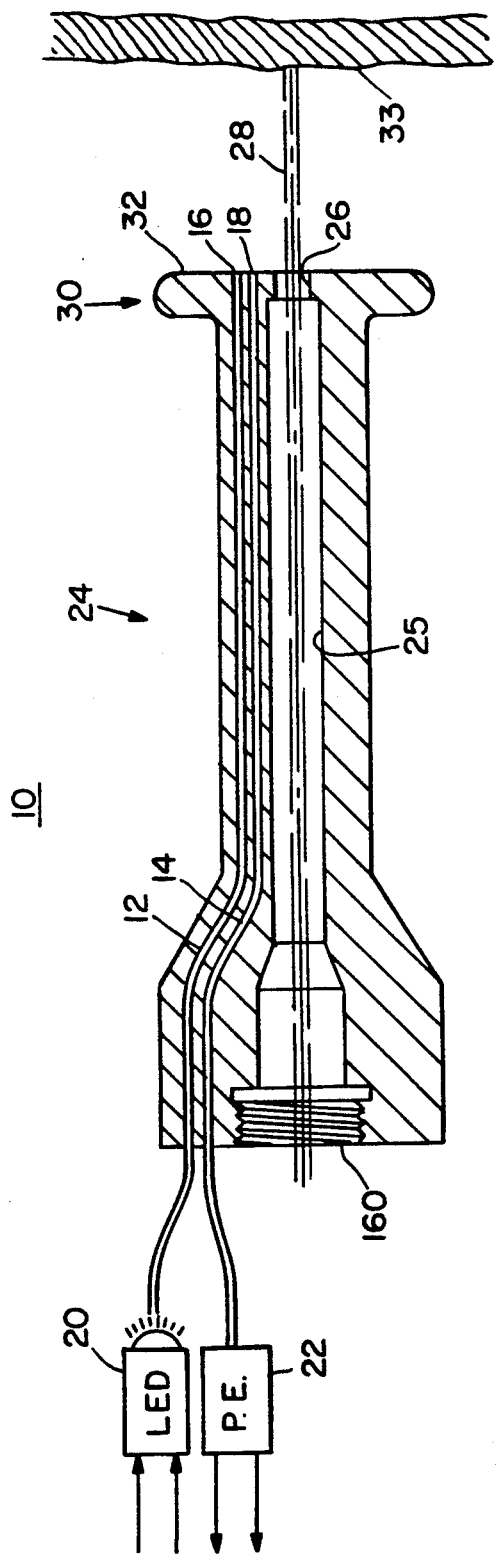
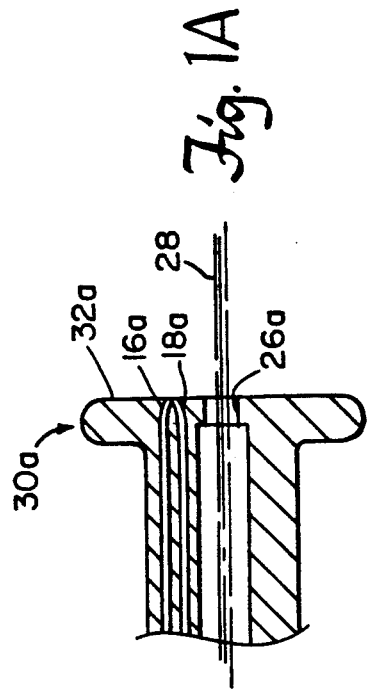
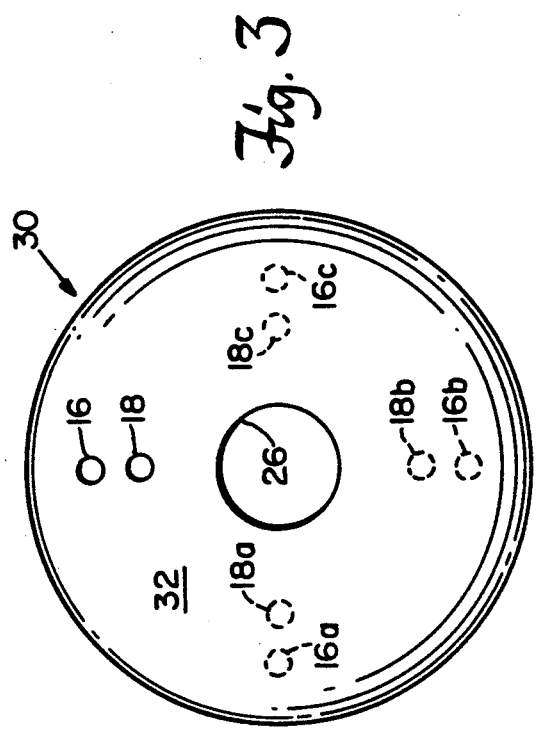

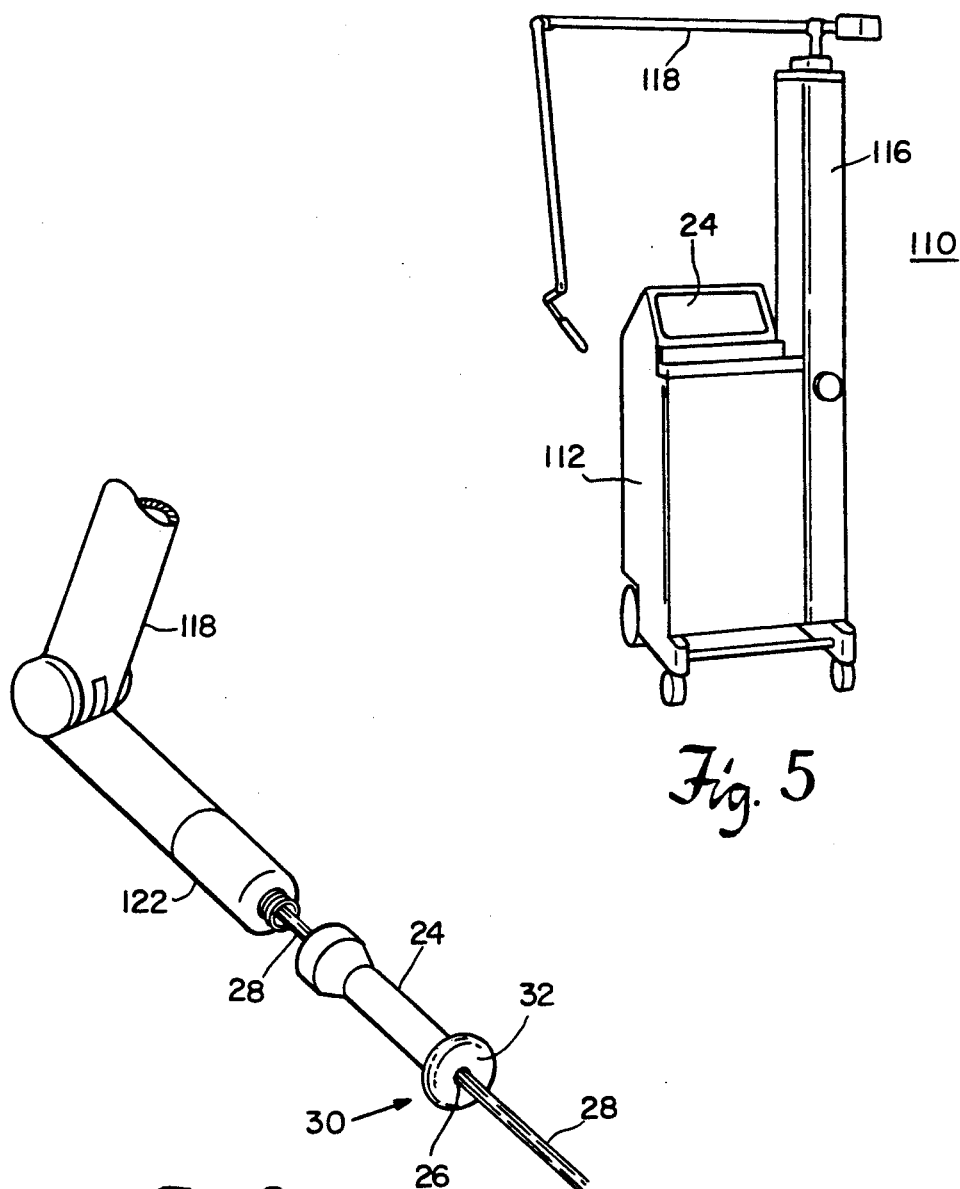
Fig. 5
Fig. 6
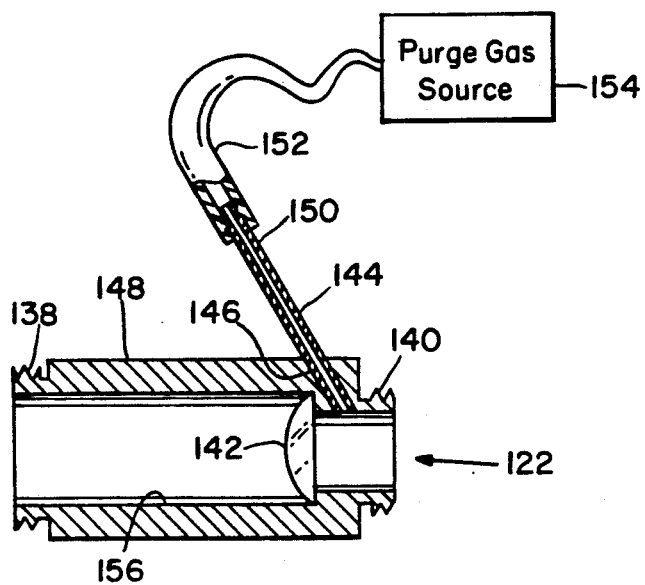
Fig. 7

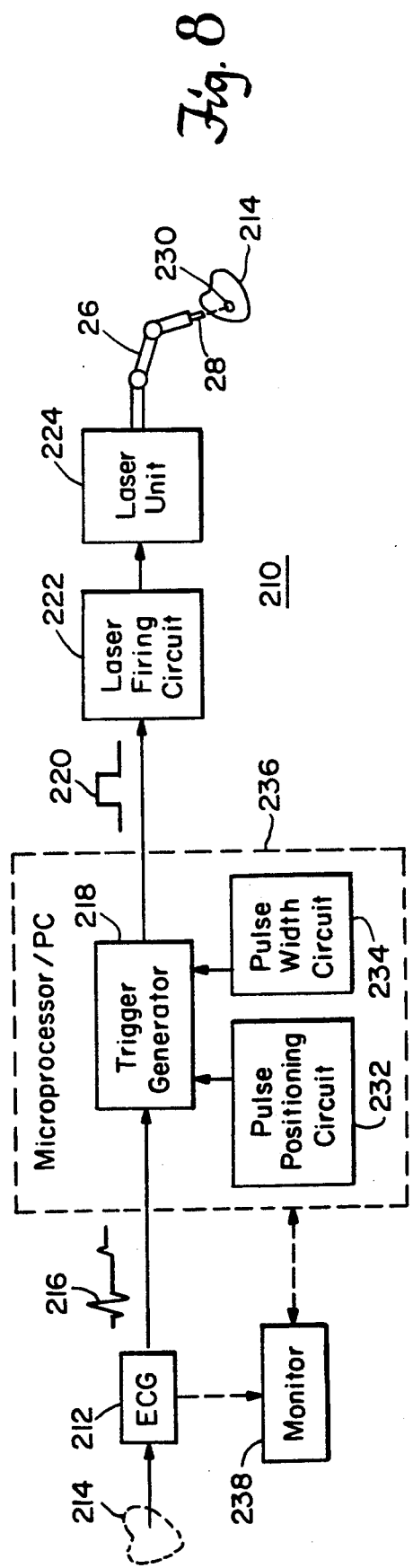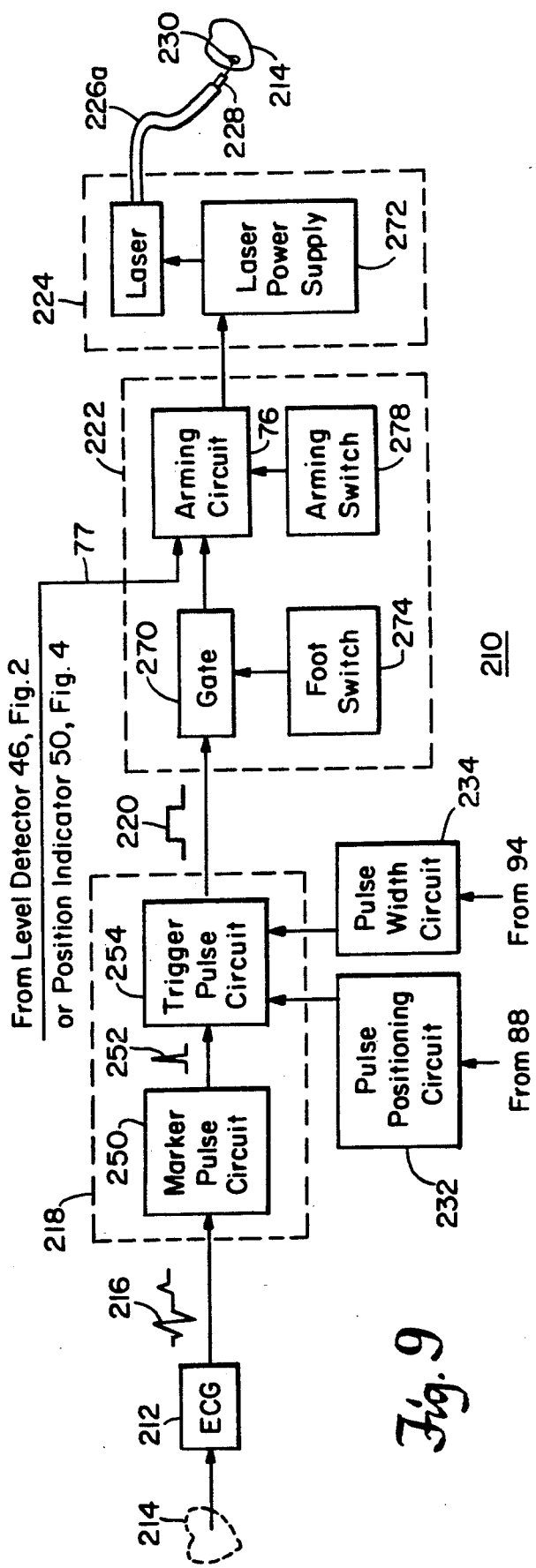

HANDPIECE OPTICAL PROXIMITY DETECTOR FOR DISABLING SURGICAL LASER BEAM

FIELD OF INVENTION

This invention relates to a proximity detector for the probe of a beam delivery apparatus of a laser system, and more particularly to such a proximity detector which determines the position of the probe relative to a target surface without additional interference with that surface.

BACKGROUND OF INVENTION

As more and more powerful lasers are adapted for practical uses such as surgery, it has become more and more important to ensure against accidental firing of the laser. This is particularly so in surgical laser applications where misfiring could cause serious damage to patients and medical personnel alike. Often, in surgical protocols lasers are only to be fired when the probe or handpiece or other part of the laser beam delivery system is in contact with the body part to be operated on. Detection of contact can be a difficult matter. In laser heart surgery, for example, electrical or even magnetic proximity detectors can interfere with the electric field of the heart and cause problems with the heart function and rhythm; mechanical sensors likewise can cause reflex reactions by the heart which can result in arrhythmia. Thermal detectors are ineffective, where, also as in heart surgery, body parts are chilled before surgery. Further, in thermal sensor devices it is possible that ambient heating could cause accidental firing of the laser.

SUMMARY OF INVENTION

It is therefore an object of this invention to provide an improved proximity detector for a probe for a laser beam delivery apparatus.

It is a further object of this invention to provide such a proximity detector which prevents firing of the laser unless the probe is in the proper position with respect to the target surface.

It is a further object of this invention to provide such a proximity detector which prevents firing of the laser unless the probe is contacting the target surface.

It is a further object of this invention to provide such a proximity detector which does not effect electrical, magnetic or physical interference with the target surface.

It is a further object of this invention to provide such a proximity detector which determines the orientation of the probe face relative to the target surface.

It is a further object of this invention to provide such a proximity detector which non-invasively, non-interferingly determines the position of the probe or handpiece during heart or other laser surgery operations.

The invention results from the realization that a safer and more accurate laser system can be achieved using a proximity detector which prevents firing of the laser system when the handpiece or probe of the beam delivery apparatus senses an improper position including distance and/or orientation of the probe face with respect to the target surface.

This invention features a proximity detector for the probe of the beam delivery apparatus of a laser system. The probe has a face for confronting a target surface to be struck by the laser beam. There are means for directing a gauging light to the target surface and means for sensing the gauging light returning from the target surface to the probe. Means responsive to the means for sensing generates a control signal representative of the position of the pulse of the probe relative to the surface in order to enable the laser system to fire.

In a preferred embodiment the gauging light is a visible light. The means for directing may include a light source, and a first aperture in the probe face. There may be a fiber optic element extending between the light source and the aperture. The means for sensing may include a photodetector means and a second aperture in the probe face, and there may be fiber optic means extending between the photodetector means and the second aperture. The means for generating may include a level detector for indicating that the amount of light returning from the target surface has exceeded a predetermined level. The means for directing may include means for modulating the light source, and the means for sensing may include a photodetector and a phase detector, responsive to the photodetector and the means for modulating, for determining the level of the light returning from the surface. There may be a plurality of means for directing and of means for sensing, and there may be means responsive to those means for directing and sensing for indicating that the probe face is tilted relative to the target surface.

DISCLOSURE OF PREFERRED EMBODIMENT

Other objects, features and advantages will occur to those skilled in the art from the following description of a preferred embodiment and the accompanying drawings, in which:

FIG. 1 is a cross-sectional view of a handpiece or probe for a laser beam delivery apparatus employing the proximity detector of this invention;

FIG. 1A is an enlarged cross-sectional view of the handpiece of FIG. 1 with an alternative arrangement of the light source and sensing fiber optic elements;

Figure 2:
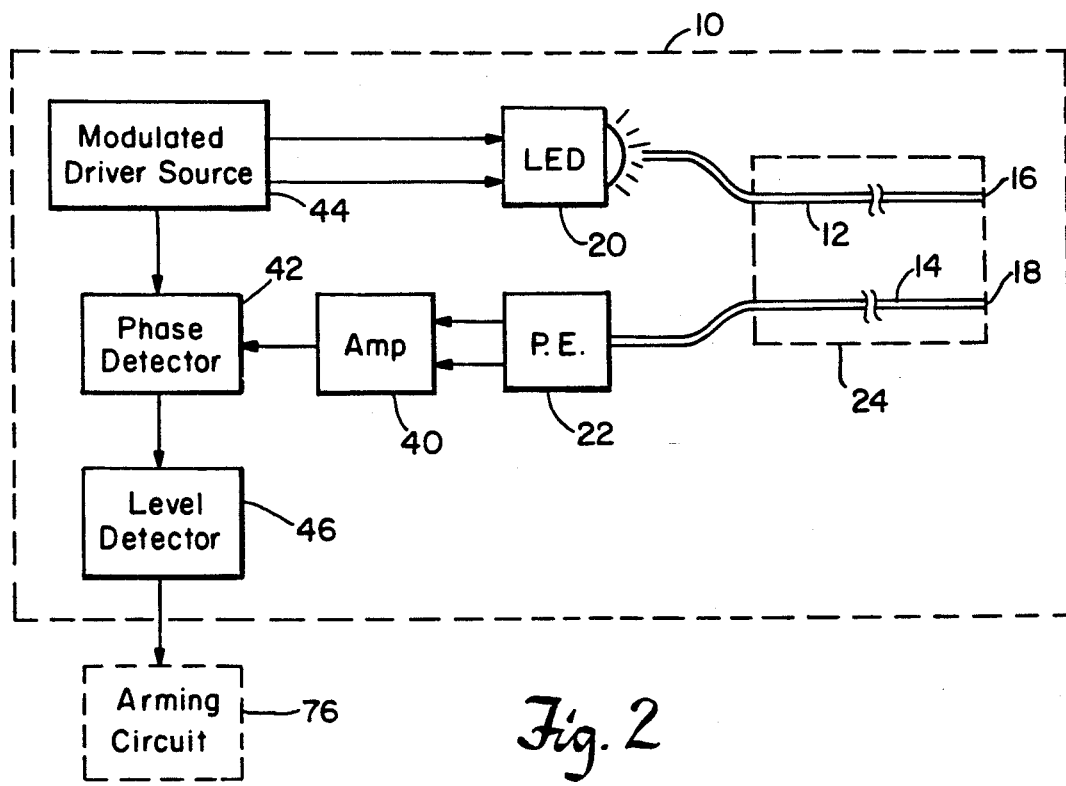
FIG. 2 is a schematic block diagram of the proximity detector according to this invention which generates a signal to enable the arming circuit of a laser system.
Figure 4:
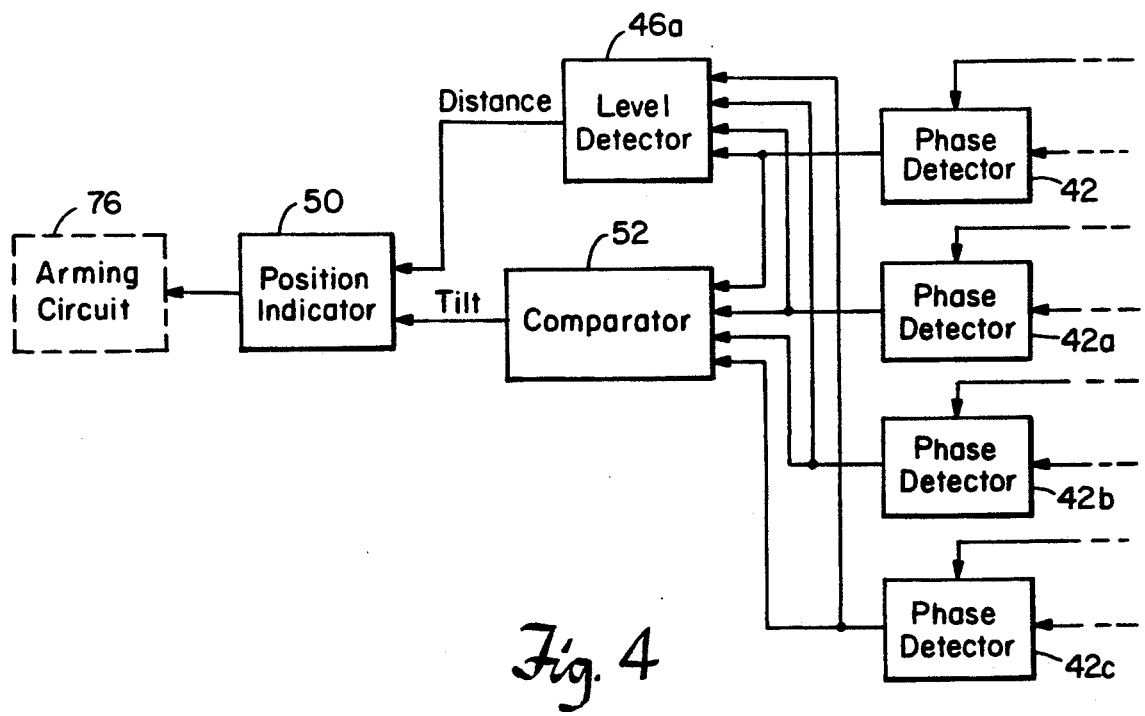

FIG. 3 is a front elevational view of the face of the probe of FIG. 1 showing a pair of apertures forming a part of the proximity detector according to this invention and three additional pairs of such apertures shown in phantom which can be used to determine orientation as well as the distance of the probe from the target surface; and FIG. 4 is a schematic block diagram for determining the distance and the orientation of the probe face relative to the target surface, as well as providing an enabling signal to an arming circuit in the associated laser system;

FIG. 5 is a three-dimensional view of a $CO_2$ surgical laser system employing the proximity detector of this invention;

FIG. 6 is an enlarged view of a proximity detector according to this invention and a portion of the probe and articulated optical arm which carries it;

FIG. 7 is is an enlarged cross-sectional view of the focusing lens section of the probe of FIGS. 1 and 2;

FIG. 8 is a schematic block diagram of a heart-synchronized pulsed laser system using the proximity detector according to this invention; and FIG. 9 is a more detailed diagram of the system of FIG. 1.

There is shown in FIG. 1 a proximity detector 10 according to this invention which includes a pair of fiber optic elements 12 and 14 having apertures 16 and 18 at one end and at their other ends being associated with a light source, LED 20, and a photodetector cell 22. Fiber optic elements 12 and 14 are mounted in handpiece or probe 24, which has at its distal end 30 a broad face 32 in which apertures 16 and 18 are located. The laser beam 28 passes through bore 25 on its way through hole 26 to strike target surface 33. The gauging light from light source LED 20 is propagated through fiber optic element 12 to aperture 16 From aperture 16 the light strikes target surface 33. The returning light, both scattered and reflected, is sensed at aperture 18 and delivered by fiber optic element 14 to photodetector element 22. When probe face 32 is against target surface 33, there will be no returning light at aperture 18, and as face 32 is moved away from target surface 33 the increasing space permits more and more light, up to a point, to be returned to aperture 18.

Alternatively, fiber optic elements 16a, 18a, FIG. 1A, can be arranged to converge at face 32a so that as the end 30 approaches the surface of the heart the signal gets stronger and stronger and reaches a maximum when face 32a contacts the heart.

The signal generated by photodetector 22 from the returning light is directed to amplifier 40, FIG. 2, after which it is submitted to phase detector 42. Light source 20 is driven by the modulator driver source 44 and phase detector 42 is tuned to discriminate only the modulated light. This is done in order to avoid ambient light conditions from interfering with the system. The difference between the phase of the returning light on fiber optic element 14 and the emitted light on fiber optic element 12 is an indication of the position of the probe face 32 with respect to the target surface 33. When the returning signal reaches a predetermined magnitude, level detector 46 responds by sending a signal to arming circuit 76 to prevent the laser system from firing. In this construction if the probe face is not in direct contact with the target surface, the laser is disabled and will not be able to fire.

Although only one pair of fiber optic elements and one pair of apertures 16, 18 have been shown in FIGS. 1 and 2, this is not a necessary limitation of the invention, as two or more such pairs may be employed as indicated in phantom in FIG. 3 as 16a, 18a, 16b, 18b, and 16c, 18c. With two or more such pairs the position of face 32 with respect to surface 33 can be determined not only with respect to distance, but also orientation or tilt. Thus, as shown in FIG. 4, each of the pairs of apertures 16, 18, 16a, 18a, 16b, 18b, 16c, 18c, has a channel associated with it terminating in phase detectors 42, 42a, 42b and 42c, respectively. Each of the phase detectors provides an output to level detector 46a which provides an indication of the distance between the probe face 32 and target surface 33 to position indicator 50. Each phase detector also provides an input to comparator 52 which resolves the tilt or non-parallel condition of face 32 with respect to surface 33 and provides a tilt signal to position indicator 50. Position indicator 50 can then display to the user the distance and the tilt to permit adjustment and also provide a signal as before to the arming circuit 76 to disable the laser until the probe face is in the correct position with respect to the target surface. The circuit is shown in greater detail in U.S. patent application Ser. No. 07/586,891, filed Sep. 24, 1990, entitled "Handpiece For Transmyocardial Vascularization Heart Synchronized Pulsed Laser System", Rudko et al., LE-111J, incorporated herein by reference.

Proximity detector 10 may be used in a surgical laser system 110, FIG. 5, including a power supply 112 and control panel 114 for operating $CO_2$ laser 116, whose output beam is directed through articulated arm 118 to lens unit 122, FIG. 6, including a lens for focusing the laser beam and a probe or handpiece 24 which includes an aperture 26 through which the laser beam 28 exits. The distal end 30 of handpiece or probe 24 includes an enlarged contact surface 32 for contacting the wall of the heart to be perforated by the laser beam. Surface 32 is relatively large to minimize the contact pressure between it and the heart wall, and is flat and smooth with rounded edges to minimize interference with the heart. Surface 32 is typically 1 cm or greater in diameter.

The focusing unit or lens unit 22, FIG. 7, includes a threaded portion 138 for interconnection with arm 18, and a threaded portion 140 which interconnects with barrel 24. Carried within unit 122 is focusing lens 142. An inlet tube 144 is joined by interference fit with bore 146 and a cylindrical wall 148 of unit 122. At its free end 150, inlet 144 is connected to a hose 152 which is in turn connected to a purge gas source 154 which provides a gas such as $CO_2$ under gentle pressure to create a backflow from lens 142 forward into probe 24. This keeps any debris from the vaporization from contacting and obscuring or damaging lens 142. Lens 142 is positioned directly in line with passage 156 provided in unit 122 for propagation of the laser beam. Threads 140 of lens unit 122 engage with threads 160, FIG. 1, of probe 24. Lens 42 focuses the laser beam proximate aperture 26 and surface 32. Although handpiece 24 engages the rest of detector 10 through threads 160, 162, this is not a necessary limitation of the invention. Any suitable connection mechanism will suffice, e.g. bayonet.

The proximity detector and probe may be employed in a heart synchronized pulsed laser system such as shown in U.S. patent application Ser. No. 07/586,951, filed Sep. 24, 1990, entitled "Heart-Synchronized Pulsed Laser System", Rudko et al., LE-109J, incorporated herein by reference. Such a heart-synchronized pulsed laser system 210 includes electrocardiogram unit 212 connected to a heart 214 which is to undergo the surgery. The ECG signal 216 is delivered to trigger generator 218, which provides a trigger pulse 220 to laser firing circuit 222, which in turn energizes laser unit 224 including a laser power supply and a laser to produce a pulsed laser beam through articulated optical arm 118 into optical handpiece 24 to make a hole 230 in heart 214. The position of trigger pulse 220 in the heartbeat cycle of ECG signal 216 is determined by pulse positioning circuit 232. The width of the pulse 22 and its duration during the heartbeat cycle is determined by pulse width circuit 34. Trigger generator 218 as well as pulse positioning circuit 232 and pulse width circuit 234, may be included as an additional board in a PC or a microprocessor 236, in which case the system can be controlled through the computer keyboard and suitable software. PC 236 and ECG 212 may have separate monitors, or they may have a single monitor 238 which displays both the ECG and information about the trigger pulse 220.

Trigger generator 218 may include a marker pulse circuit 250, FIG. 9, which provides marker pulse 252 and trigger pulse circuit 254 which responds to marker pulse 252 to create trigger pulse 220. Alternatively, marker pulse circuit 250 is included in the ECG itself in some cases.

In FIG. 9, laser firing circuit 222 is shown to include gate 270 which generally inhibits the delivery of trigger circuit 20 to laser power supply 72 in laser unit 24. The inhibiting effect of gate 270 can be overcome when the surgeon steps on foot switch 274. Trigger pulse 220 is still inhibited, however, by arming circuit 76 which in turn can have its inhibiting effect overcome by the operation of arming switch 278. This double lock on the delivery of trigger pulse 220 to laser power supply 272 ensures that the firing of the laser is truly desired and not accidental. Thus the surgeon must first arm the system by operating arming switching 278 to enable arming circuit 76. Arming circuit 76 also receives a signal on line 77 from level detector 46, FIG. 2, or from position indicator 50, FIG. 4, to prevent enablement of arming circuit 76 unless the probe is properly positioned relative to the target surface 33. Then and only then is the next occurring trigger pulse 220 able to pass through gate 270 to the laser power supply 272 by actuation of foot switch 274. Also included in laser unit 224 is a standard $CO_2$ laser 280. The output of laser 280 may be delivered through a fiber optic element 226a to handpiece 24.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A proximity detector for the probe of the beam delivery apparatus of a laser system comprising:
   a probe having a face for contacting a target surface to be struck by the laser beam;
   means for directing a gauging light to said target surface;
   means for sensing any gauging light returning from said target surface to said probe; and
   means, responsive to said means for sensing, for generating a control signal inhibiting the firing of the laser system if gauging light returning from said target is sensed by said means for sensing.

2. The proximity detector of claim 1 in which said gauging light is visible light.

3. The proximity detector of claim 1 in which said means for directing includes a light source.

4. The proximity detector of claim 3 in which said means for directing includes a first aperture in said probe face.

5. The proximity detector of claim 4 in which said means for directing includes fiber optic means extending between said light source and aperture.

6. The proximity detector of claim 1 in which said means for sensing includes a second aperture in said probe face.

7. The proximity detector of claim 6 in which said means for sensing includes a photodetector means.

8. The proximity detector of claim 7 in which said means for sensing includes a fiber optic means extending between said photodetector means and said second aperture.

9. The proximity detector of claim 3 in which said means for directing includes means for modulating said light source.

10. The proximity detector of claim 9 in which said means for sensing includes photodetector means and phase detector means, responsive to said photodetector means and said means for modulating, for determining the level of the light returning from said surface.

11. The proximity detector of claim 1 further including a plurality of means for directing and of means for sensing and means, responsive to said means for directing and means for sensing, for indicating that said probe face is tilted relative to said target surface.

12. A proximity detector for the probe of a beam delivery apparatus of a laser system including a laser arming circuit comprising:
   a probe having a face for contacting a target surface to be struck by the laser beam;
   means for directing a gauging light to said target surface;
   means for sensing any gauging light returning from said target surface to said probe; and
   means for sending a signal to said arming circuit when said means for sensing senses gauging light returning from said target surface to said probe.

* * * * *